United States Patent
Ohashi et al.

(10) Patent No.: US 7,090,665 B2
(45) Date of Patent: Aug. 15, 2006

(54) DISPOSABLE DIAPER

(75) Inventors: Naoto Ohashi, Kagawa-ken (JP); Yoshio Ono, Kagawa-ken (JP); Toru Oba, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 09/997,652

(22) Filed: Nov. 29, 2001

(65) Prior Publication Data

US 2002/0065499 A1    May 30, 2002

(30) Foreign Application Priority Data

Nov. 30, 2000  (JP) .............................. 2000-366047

(51) Int. Cl.
*A61F 13/15*  (2006.01)
*A61F 13/20*  (2006.01)

(52) U.S. Cl. .......................... 604/385.14; 604/385.01; 604/385.03; 604/385.11; 604/387; 604/394

(58) Field of Classification Search ......... 604/385.201, 604/364–366, 378–380, 383–384, 385.01, 604/385.03, 385.101, 385.14, 387, 393–399
See application file for complete search history.

(56) References Cited

U.S. PATENT DOCUMENTS

| | | | |
|---|---|---|---|
| 2,566,325 A | | 9/1951 | Ganz |
| 2,788,003 A | * | 4/1957 | Morin .......................... 604/366 |
| 2,896,618 A | * | 7/1959 | Schaefer ....................... 602/47 |
| 3,211,147 A | * | 10/1965 | Pherson ........................ 604/364 |
| 3,430,630 A | * | 3/1969 | Megison et al. ............. 604/365 |
| 3,442,268 A | * | 5/1969 | Bird ............................ 604/380 |
| 3,721,242 A | * | 3/1973 | Krusko ........................ 604/365 |
| 3,769,978 A | * | 11/1973 | DeNight et al. ............. 604/374 |
| 3,886,941 A | * | 6/1975 | Duane et al. ................. 604/370 |
| 3,908,659 A | | 9/1975 | Noel et al. |
| 3,993,820 A | * | 11/1976 | Repke .......................... 428/167 |
| 4,022,210 A | * | 5/1977 | Glassman ..................... 604/394 |
| 4,072,150 A | * | 2/1978 | Glassman ..................... 604/389 |
| 4,074,721 A | * | 2/1978 | Smits et al. .................. 604/366 |
| 4,176,667 A | * | 12/1979 | Herring ........................ 604/368 |
| 4,443,512 A | | 4/1984 | Delvaux |
| 4,615,695 A | * | 10/1986 | Cooper ..................... 604/385.15 |
| 4,650,481 A | * | 3/1987 | O'Connor et al. .......... 604/380 |
| 5,069,676 A | * | 12/1991 | Ito et al. ...................... 604/358 |
| 5,128,193 A | * | 7/1992 | Anapol et al. .............. 428/171 |

(Continued)

FOREIGN PATENT DOCUMENTS

| | | | |
|---|---|---|---|
| EP | 0136524 A1 | * | 4/1985 |
| EP | 0238334 A1 | * | 9/1987 |
| EP | 0313766 A2 | * | 5/1989 |

(Continued)

OTHER PUBLICATIONS

American Heritage Dictionary, 1 pg, definition of "grid".*

*Primary Examiner*—Tatyana Zalukaeva
(74) *Attorney, Agent, or Firm*—Butzel Long

(57) ABSTRACT

A disposable diaper that includes a cover member and a body fluid absorbent member attached to an inner side of the cover member. The absorbent member is composed of a liquid-pervious topsheet, a backsheet and an absorbent core member disposed therebetween. The absorbent member is formed on a side adjacent the backsheet with at least one first groove concaved in a direction from the backsheet toward the topsheet.

9 Claims, 11 Drawing Sheets

U.S. PATENT DOCUMENTS

| | | | |
|---|---|---|---|
| 5,514,104 A * | 5/1996 | Cole et al. | 604/366 |
| 5,514,120 A * | 5/1996 | Johnston et al. | 604/378 |
| 5,681,300 A * | 10/1997 | Ahr et al. | 604/367 |
| 5,846,231 A * | 12/1998 | Fujioka et al. | 604/380 |
| 5,891,118 A * | 4/1999 | Toyoshima et al. | 604/366 |
| 5,938,651 A * | 8/1999 | Widlund et al. | 604/373 |
| 6,506,961 B1 * | 1/2003 | Levy | 604/380 |
| D473,302 S * | 4/2003 | Harriz et al. | D24/125 |

FOREIGN PATENT DOCUMENTS

| | | |
|---|---|---|
| EP | 0 441 064 | 8/1991 |
| EP | 0613671 A2 * | 9/1994 |
| GB | 2319730 A * | 6/1998 |
| JP | 8-38546 | 2/1996 |
| JP | 8-280739 | 10/1996 |
| JP | 1016115 A * | 1/1998 |

* cited by examiner

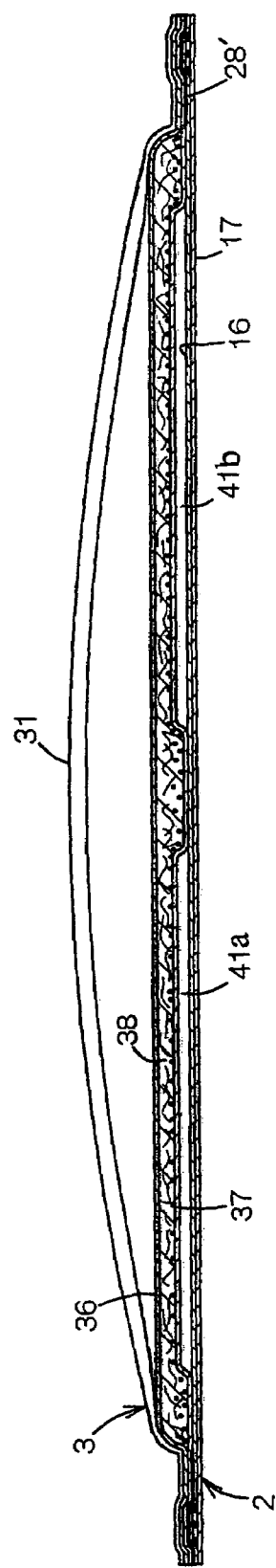

DISPOSABLE DIAPER

BACKGROUND OF THE INVENTION

This invention relates to a disposable diaper for absorption and containment of excrement.

Japanese Patent Application Publication No. 1996-280739A describes a disposable diaper comprising a pants-shaped outer sheet and an absorbent panel attached to an inner surface of the outer sheet. The absorbent panel longitudinally extends across a crotch region of the outer sheet into front and rear waist regions. This absorbent panel comprises a liquid-pervious sheet, a liquid-impervious sheet and an absorbent member disposed between these two sheets. When this disposable diaper is worn by a wearer, the outer sheet which is elastically stretchable in a direction surrounding the wearer's waist region causes the absorbent panel to fit close to the wearer's body.

Japanese Patent Application Publication No. 1996-38546A describes a pants-type disposable diaper provided on an inner side of the pants with an absorbent pad structure which longitudinally extends across a crotch region of the pants into front and rear waist regions. This absorbent pad structure comprises a liquid-pervious topsheet, a liquid-impervious backsheet and an absorbent member disposed between these two sheets. When this diaper is worn, elastically stretchable side sheets provided on the pants cause the absorbent pad structure to fit close to the wearer's body.

In diapers that generally comprise a pants-type cover member and a body fluid absorbent member attached to an inner side of the cover member, like those described in the above Publications, the absorbent member has a liquid-pervious topsheet intended to be fit to a wearer's skin, a backsheet opposed to the topsheet and an absorbent core disposed between these two sheets wherein the backsheet is covered with the pants-type cover member. When such a diaper is worn, the pants-type cover member is pressed against the backsheet of the absorbent member which is thereby pressed against a wearer's skin. In this manner, the backsheet of the absorbent member is covered with the relatively thick pants-type cover member, so air permeability of the diaper may be reduced even if an air permeable and liquid-impervious sheet is used as the backsheet. As a result, the wearer's skin against which this absorbent member is pressed may suffer from an uncomfortable stuffiness. Such a problem may occur not only with a pants-type cover member but also with an open-type cover member.

SUMMARY OF THE INVENTION

It is an object of this invention to provide a disposable diaper having improved air permeability which disposable diaper comprises a cover member adapted to cover front and rear waist regions as well as a crotch region of a wearer's body, and an absorbent member adapted to be attached to an inner side of the cover member.

According to this invention, there is provided a disposable diaper comprising a cover member composed of front and rear waist regions and a crotch region and a body fluid absorbent member attached to an inner side of the cover member.

In one embodiment of this invention, the body fluid absorbent member extends in a longitudinal direction across the crotch region into the front and rear waist regions and has front and rear end portions that are fixed to an inner surface of the cover member at the front and rear end portions of the cover member. The body fluid absorbent member includes a liquid-pervious topsheet that is placed against the wearer's body, a backsheet that is placed against the inner surface of the cover member and a body fluid absorbent core disposed between these two sheets. A side of the absorbent core facing the backsheet is formed with a plurality of grooves that are concaved in a direction extending from the backsheet toward the topsheet. The grooves extend in one of the longitudinal direction and a direction that is orthogonal to the longitudinal direction.

BRIEF DESCRIPTION OF THE DRAWINGS

FIG. 11 is a sectional view similar to FIG. 6 which uses a pressure-sensitive adhesive to detachably fix the body fluid absorbent member to the cover member.

DETAILED DESCRIPTION OF THE PREFERRED EMBODIMENTS

Details of a disposable diaper according to this invention will be more fully understood from the description given hereunder with reference to the accompanying drawings.

Figure 1:
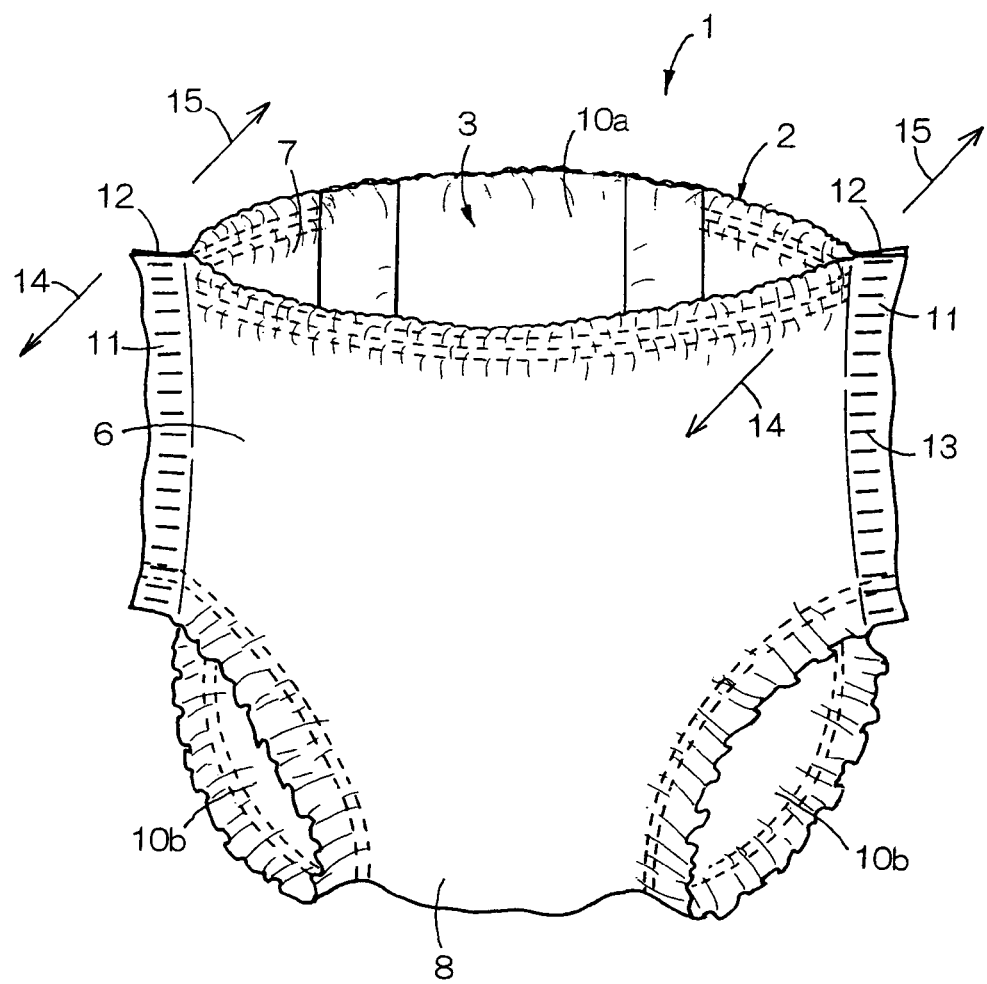
FIG. 1 is a perspective view showing one embodiment of a disposable diaper according to this invention.

A disposable diaper 1 shown in FIG. 1 in a perspective view is of a pants-type and comprises a pants-type cover member 2 adapted to cover a wearer's waist regions and crotch region and a body fluid absorbent member 3 attached to an inner side of the cover member 2. The cover member 2 is composed of a front waist region 6, a rear waist region 7 and a crotch region 8 positioned between these two waist regions 6, 7. The front and rear waist regions 6, 7 are overlaid upon and joined to each other along transversely opposite side edge portions 11, 12, at a plurality of joining zones 13 arranged intermittently in a longitudinal direction of the diaper 1 along the respective side edge portions 11, 12. Such diaper 1 has a waist-opening 10a and a pair of leg-openings 1ob of which respective peripheral edge portions are provided with elastic members 22, 23 (See FIG. 2 also) as indicated by chain lines.

Figure 2:
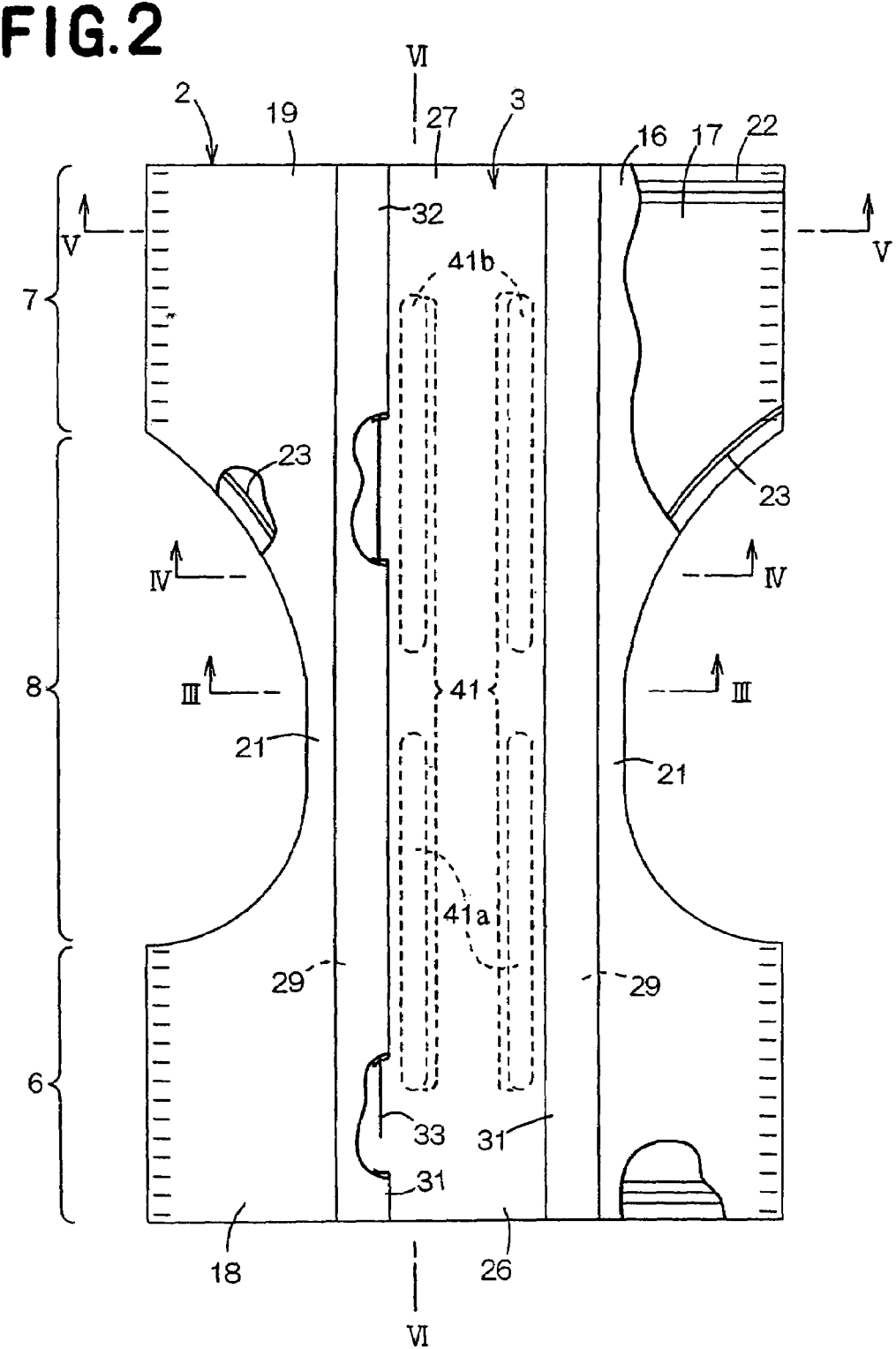
FIG. 2 is a partially cutaway plan view showing the disposable diaper as having been unfolded.

FIG. 2 is a plan view of the diaper 1 in which the side edge portions 11, 12 connecting the front and the rear waist regions 6, 7 to each other have been separated from one another with the diaper 1 having been unfolded in opposite directions as indicated the diaper 1 unfolded in this manner, the cover member 2 has an hour glass shape in comprises an inner sheet 16 and an outer sheet 17 which are identical in shape as well as size and which are intermittently bonded to each other by means of appropriate adhesive such as a hot melt adhesive or a welding technique. Elastic members 22 associated with the waist-opening and elastic members 23 associated with the respective leg-openings are attached under tension to an inner surface of the inner sheet 16 or an inner surface of the outer sheet 17 along longitudinally opposite end portions 18, 19 of the front and rear waist regions 6, 7 and along transversely opposite side edge portions 21 of the crotch region 8, of the cover member 2 respectively. The absorbent member 3 extends longitudinally across the crotch region 8 into the front and rear waist regions 6, 7 of the cover member 2 and has front and rear end portions 26, 27, which are bonded to the end portions 18, 19 of the front and rear waist regions 6, 7 bu means of hot melt adhesive 28 (See FIG. 6). FIG. 11 depicts an alternative embodiment of the present invention in which the front and rear end portions 26, 27 are detachably attached to end portions 18, 19 by other means such as a pressure-sensitive adhesive 28'. In other embodiments a mechanical fastener well known under the trade name of MAGICTAPE can be used to detachably attach the front and rear end portions 26, 27 to end portions 18, 19. Transversely opposite side edge portions 29 of the absorbent member 3 extending between the front and rear end portions 26, 27 are provided with leak-barrier cuffs 31 which have openings toward a transversely middle zone of the absorbent member 3. Elastic members 33 extending between the front and rear end portions 26, 27 are attached under tension to inner edge portions 32 of the leak-barrier cuffs 31. The absorbent 3 is, as indicated by chin lines in FIG. 2, formed on its backsheet 37 with first grooves 41 (See FIG. 4). As depicted in FIG. 2, each of the first grooves 41 consists of a first segment 41a that extends to the crotch region 8 and the front waist region 6 and a second segment 41b that extends in the crotch region 8 and the rear waist region 7, the first and the second segments 41a and 41b of each first groove 41 being aligned with one another longitudinally and being excluded from extending across longitudinal center of the crotch region 8 of the diaper and being excluded from extending into the front and rear end portions 26 and 27 of the diaper.

Figure 3:
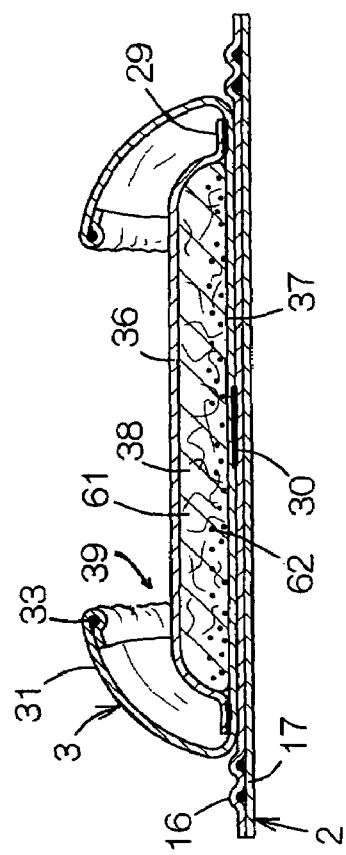
FIG. 3 is a sectional view taken along a section line III—III in FIG. 2.
Figure 4:
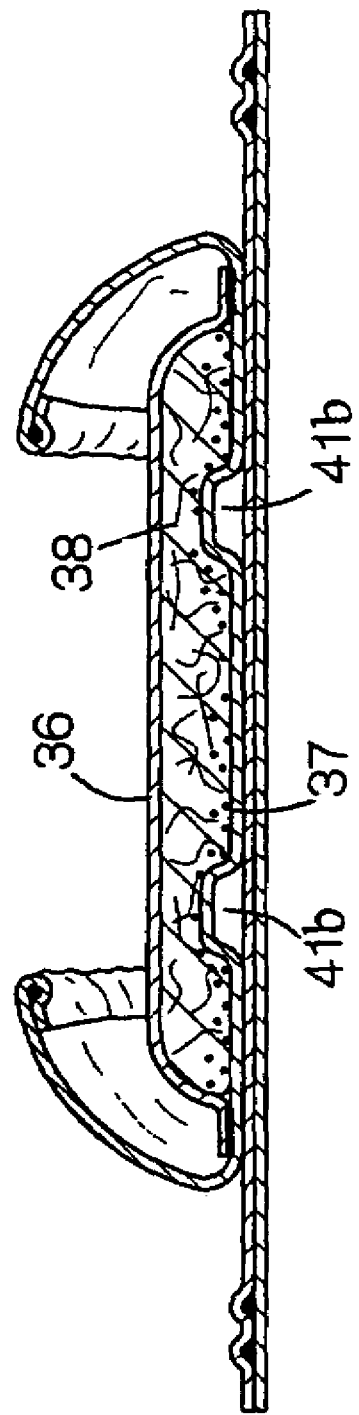
FIG. 4 is a sectional view taken along a section line IV—IV in FIG. 2.
Figure 5:
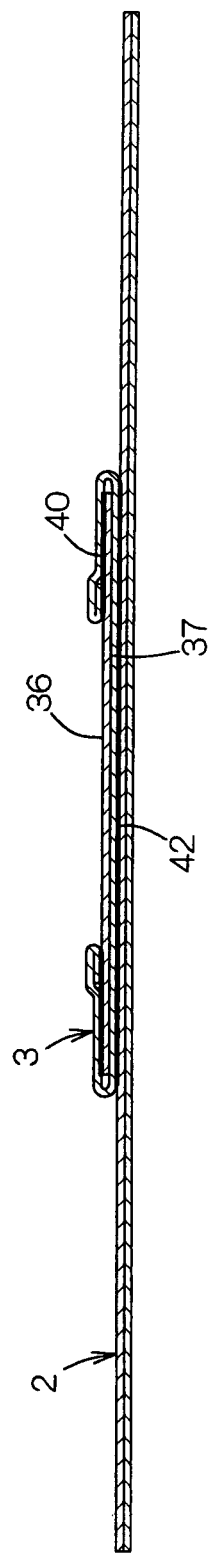
FIG. 5 is a sectional view taken along a section line V—V in FIG. 2 that is not partially cutaway.

FIGS. 3 through 5 are sectional views taken along section lines III—III, IV—IV and V—V extending in the transverse direction, respectively, in FIG. 2, with FIG. 5 not being cutaway as is FIG. 2. Referring to FIG. 3 which shows the diaper 1 in a sectional view taken along the section line III—III extending across the crotch region 8 and bisecting the diaper 1 into front and rear halves, the absorbent member 3 comprises a liquid-pervious topsheet 36 destined to contact with the wearer's skin, the previously described backsheet 37 which is preferably liquid-impervious and destined to contact with the inner sheet 16 of the cover member 2, and a body fluid absorbent core 38 disposed between the top- and backsheets 36, 37. The core 38 contains hydrophilic fibers 61 and superabsorbent polymer particles 62 and longitudinally extends toward the front and rear end portions 26, 27 of the absorbent member 3 and has a rectangular shape. The top- and backsheets 36, 37 extend outwardly beyond a peripheral edge of the core 38 and are joined together in a water-tight manner using an appropriate adhesive or a welding technique. Along the opposite side edge portions 29 of the absorbent member 3 the backsheet 37, which is joined with the topsheet 36, extends outwardly beyond the side edges of the topsheet 36 and the extensions of the backsheet 37 are folded inwardly in the transverse direction of the absorbent member 3 forming the respective leak-barrier cuffs 31. Portions of these leak-barrier cuffs 31 lying on the front and rear end portions 26, 27 of the absorbent member 3 are joined to these front and rear end portions 26, 27 using an adhesive 40 or a welding technique. In a state in which the absorbent member 3 is longitudinally curved in a U-shape configuration (See FIG. 1), contraction of elastic members 33 associated with the leak-barrier cuffs 31 causes the leak-barrier cuffs 31 to rise and form openings 39 which are oriented toward the transversely middle zone of the absorbent member 3. In this transversely middle zone, the backsheet 37 is bonded to an inner surface of the cover member 2 by means of adhesive 30.

Now referring to FIG. 4 which shows the diaper 1 in a sectional view taken along the section line IV—IV which is nearer to the rear waist region 7 than the section line III—III which divides the diaper 1 into front and rear sections as viewed in the longitudinal direction as indicated in FIG. 2, the absorbent member 3 is formed on the side of the backsheet 37 with a pair of first grooves 41 (See FIG. 4) that are concaved toward the topsheet 36 and extend longitudinally toward the front and rear end portions 26, 27. Each of the first grooves 41 preferably has a width of about 2–20 mm and a depth corresponding to about ¼–¾ of the thickness of the core 38, and each of the first grooves 41 has an inner side that is lined with the backsheet 37. The core 38 is disposed between the backsheet 37 which defines the inner side of the respective first grooves 41 and the topsheet 36 which is opposed to the backsheet 37. The first grooves 41 are intended to maintain clearance spaces between the absorbent member 3 and the member 2, which clearance spaces serve to improve permeability of the diaper 1 even when these members 2, 3 are brought into a close contact with one another.

Referring to FIG. 5 which shows the diaper 1 in a sectional view taken along the section line V—V extending in the transverse direction along the end portion 19 of the cover member 2 as indicated in FIG. 2 (without the cutaway portion), the portions of the top- and backsheets 36, 37 extending outwardly beyond the peripheral edge of the core 38 are overlaid and bonded to the cover member 2 using an adhesive 42 or a welding technique. It is also possible to attach these overlaying top- and backsheets 36, 37 in a detachable manner to the cover member 2 using an appropriate means such as pressure-sensitive adhesive.

Figure 6:
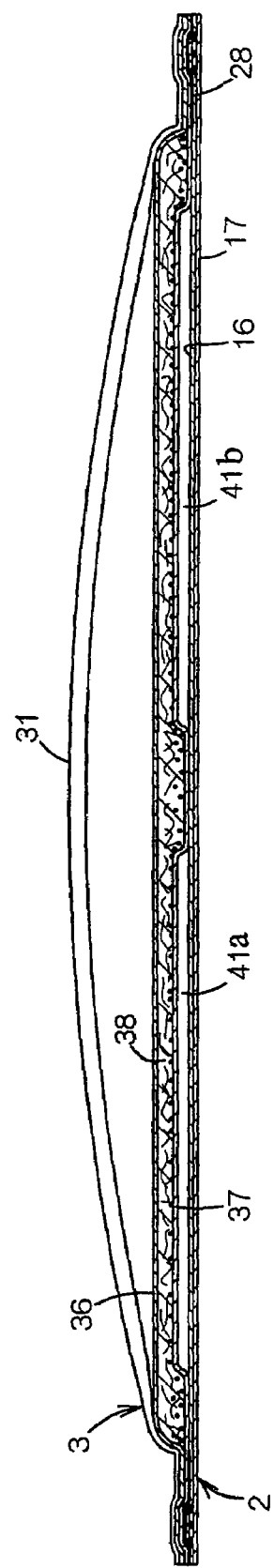
FIG. 6 is a sectional view taken along a section line VI—VI in FIG. 2.

Referring to FIG. 6 which shows the diaper 1 in a sectional view taken along the section line VI—VI extending between the front and rear end portions 18, 19 of the cover member 2 as indicated in FIG. 2 the first and second segments 41a and 41b of each of the first grooves 41 are separated respectively in the crotch region 8 in the longitudinal direction by an appropriate spacing. If necessary, it is also possible to form all of the first grooves 41 so that they are connected and continuous, rather than being separated in the longitudinal direction. It should be understood that, while the leak-barrier cuffs 31 are normally folded down onto the topsheet 36, the leak-barrier cuffs 31 are illustrated in FIG. 6 as being raised somewhat in order that the presence of these leak-barrier cuffs 31 can be seen.

When the diaper 1 of such a structure is worn, the cover member 2 and the absorbent member 3 are maintained in a spaced apart relationship from each other along the first grooves 41 even when these members 2, 3 are brought into a close contact with each other. Accordingly, air permeability between the interior and the exterior of the absorbent member 3 can be improved. For example, an air permeable and liquid-impervious sheet may be used as a stock material for the backsheet 37 of the absorbent member 3 to ensure that a flow of air high in temperature and humidity can be guided from the interior of the core 38 through the backsheet 37 into the first grooves 41 and freely moved therein without being hindered by the cover member 2. With the inner and outer sheets 16, 17 of the cover member 2 being air permeable, a flow of air high in temperature and humidity introduced into the first grooves 41 can be exhausted therefrom outside of the diaper 1.

Figure 7:
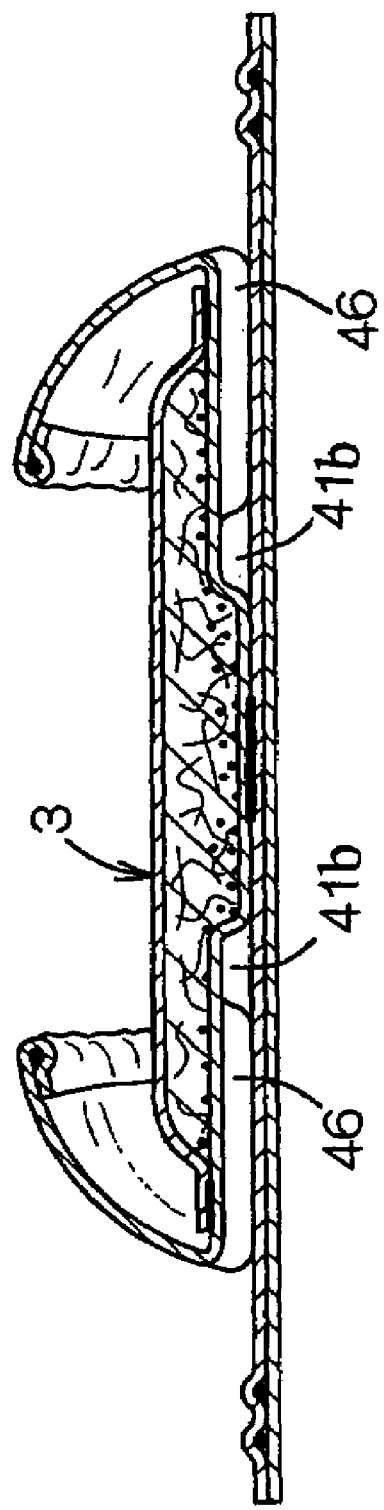
FIG. 7 is a sectional view similar to that in FIG. 4 but showing another embodiment of this invention.

FIG. 7 is a view similar to FIG. 4 but showing another embodiment of the invention. The absorbent member 3 of this embodiment of the diaper 1 is formed with, in addition to the first grooves 41 extending in the longitudinal direction, a pair of second grooves 46 extending in the transverse direction, i.e., orthogonally to the first grooves 41, between the transversely opposite side edge portions 29 of the absorbent member 3. These second grooves 46 facilitate air that is high in temperature and high in humidity to be vented from the first grooves 41 and thereby the air permeability of the absorbent member 3 is further improved. Preferably, one or more portions of the second grooves 46 having substantially the same dimensional width and depth as the first grooves 41 may intersect one portion of the first grooves 41.

Figure 8:
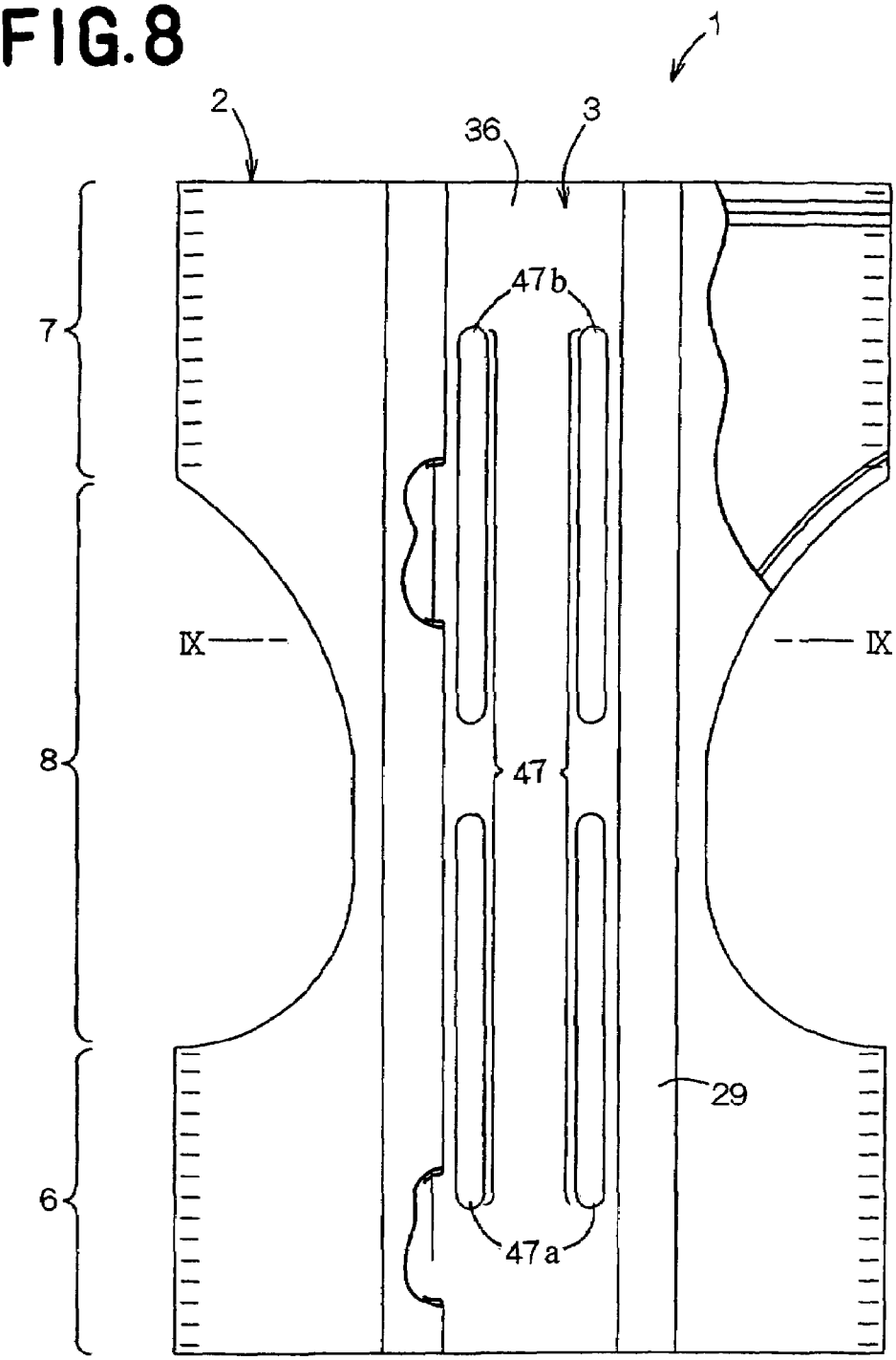
FIG. 8 is a plan view similar to that in FIG. 2 but showing still another embodiment of this invention.
Figure 9:
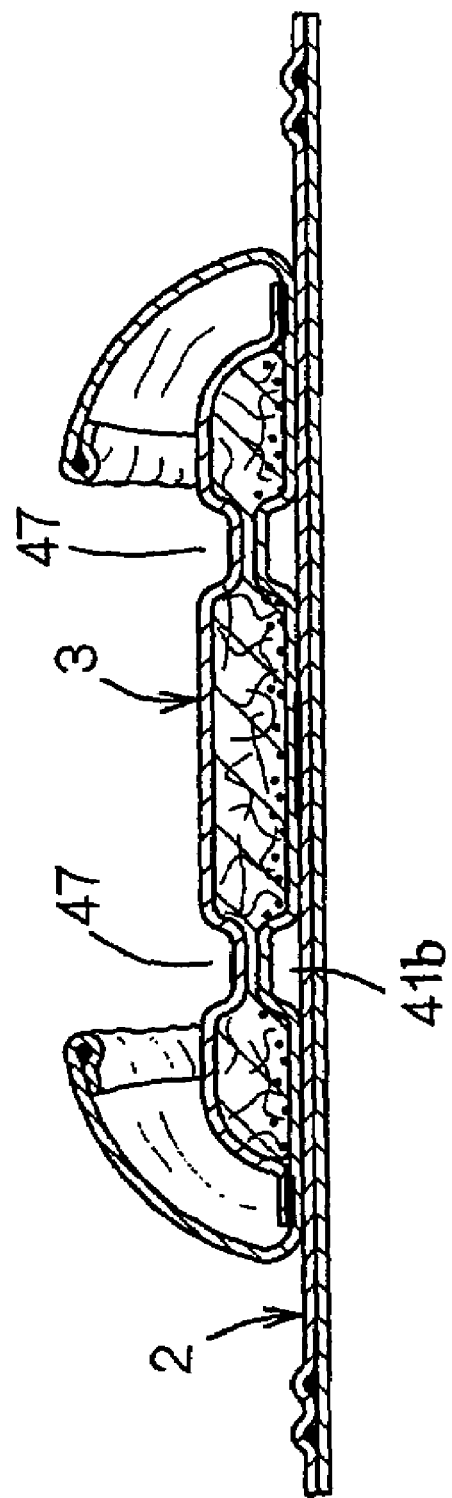
Figure 10:
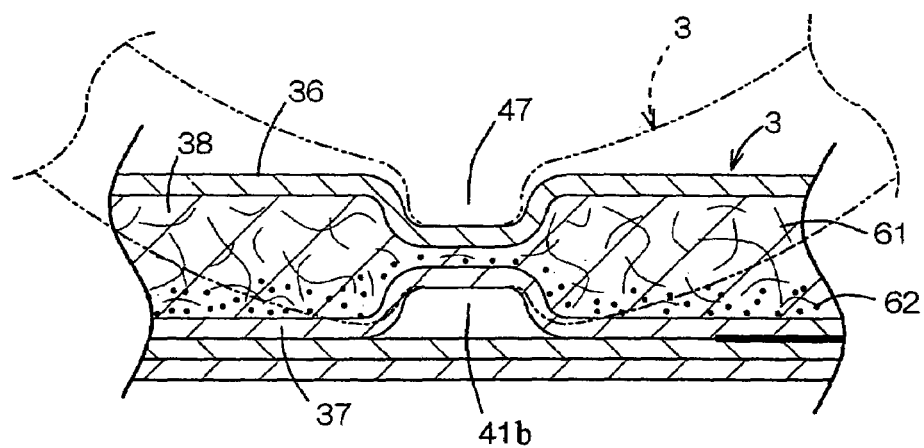

FIG. 8 is a view similar to FIG. 2 but showing still another embodiment of the invention, FIG. 9 is a sectional view taken along the section line IX—IX in FIG. 8 and FIG. 10 is an enlarged sectional view showing a portion of FIG. 9. The diaper 1 shown in FIGS. 8–10 has, in additional to the first grooves 41 or both the first and second grooves 41, 46 which are formed in the absorbent member 3 on the side of the backsheet 37, third grooves 47 formed in the absorbent member 3 on the side of the topsheet 36 so as to extend in the longitudinal direction. Preferably, the absorbent member 3 is formed on the side if the topsheet 36 with at least one portion of the third grooves 47 having an appropriate length and more preferably with at least two portions of the third grooves 47 each being spaced apart in the longitudinal direction in the crotch region 8 of the cover member 2. Referring to FIG. 8, the absorbent member 3 is formed along each of its transversely opposite side edge portions 29 with a pair of the third grooves 47 spaced form each other if the longitudinal direction. Taking account of the fact that the presence of the third grooves 47 tends to, in the same manner as the first grooves 41 in the embodiment shown by FIG. 4, restrain the absorbent member 3 from being easily curved between the front and rear end portions 26, 27, it is preferred to separate each of the third grooves 47 in the crotch region 8 so that the absorbent member 3 may be easily curved and thereby facilitated to fit to the wearer's crotch region. Each of the third groves 47 preferably has a width of about 2–20 mm and a depth corresponding to about ¼–¾ of the thickness of the core 38. The third grooves 47 formed in this manner can reduce an amount of body fluids permeated sideways and prevent body fluids from leaking sideways of the diaper 1 by introducing body fluids such as urine to be guided thereinto. As depicted in FIG. 8, each of the third grooves 47 consists of a first segment 47a that extends into the crotch region 8 and the first waist region 6 and a second segment 47b that extends into the crotch region 8 and the rear waist region 7, the first and second segments 47a and 47b of each third groove 47 being aligned with one another longitudinally and being excluded from extending across along a longitudinal center of the crotch region 8 of the diaper and being excluded from extending into the front and rear end portions 26 and 27 of the diaper.

As is apparent from FIG. 10 which shows the diaper 1 in an enlarged sectional view, the position of the third grooves 47 substantially conforms to the position of the first grooves 41 as viewed in the transverse direction of the diaper 1. With the first and third grooves 41, 47 formed in the absorbent member 3 on the side of the backsheet 37 and the side of the topsheet 36, respectively, in such an alignment, the absorbent member 3 can be curved as indicated by imaginary lines in FIG. 10 to follow a contour of the wearer's waist as the diaper 1 is worn. The first grooves 41 are deformed with their widths widened and the third grooves 47 are deformed with their widths narrowed as the absorbent member 3 follows the contour of the wearer's waist in the waist-surrounding direction. Such deformation of the grooves 41, 47 advantageously allows the absorbent member 3 to follow the contour of the wearer's waist without the formation of wrinkles on the side of the topsheet 36 even if the core 38 has a thickness of about 10–20 mm. Therefore, there is no apprehension that the presence of the topsheet 36 might cause the wearer to experience an uncomfortable feeling. In this way, the first grooves 41 which serve to improve the air permeability of the absorbent member 3 are preferably positioned with respect to the third grooves 47 so that the ability of the absorbent member 3 to fit around the wearer's waist may also be improved. More specifically, with the first grooves 41 and the third grooves 47 positioned with respect to one another as illustrated in FIG. 10, it is preferred to dispose the core 38 between the first and third grooves 41, 47 so that body fluids can be dispersed in the absorbent member 3 in the transverse direction through the core 38.

While the present invention has been described hereinabove with respect to a pants-type disposable diaper as the typical embodiment thereof, the invention is also applicable to an open-type disposable diaper. The cover member 2 may be formed from a nonwoven fabric or plastic film both of which are preferable. The core 38 of the absorbent member 3 may be formed from fluff pulp fibers 61 and superabsorbent polymer particles 62. The superabsorbent polymer particles 62 may be mixed with the fluff pulp fibers 61 and this mixture may be layered in the thickness direction of the core 38. The superabsorbent polymer particles 62 may be distributed so as to have a density that gradually increases in a direction that extends from the topsheet 36 toward the backsheet 37. FIG. 9 illustrates how the distribution density of the superabsorbent polymer particles 62 may be varied in the transverse direction of the absorbent member 3. For example, as shown in FIG. 9, the distribution density of the superabsorbent polymer particles 62 may be adjusted to be higher in a lower zone of the absorbent core 38 defined between a pair of the first grooves 41 than in an upper zone of the absorbent core 38 located above the lower zone. In any case, an amount of the superabsorbent polymer particles 62 used to form the core 38 is preferably about 2–98% by weight of the core 38. Thermoplastic synthetic fibers having a melting point of 100° C.±20° C. may be mixed into the core material up to 20% by weight to facilitate formation of the first–third grooves 41, 46, 47 by heating the core 38 under pressure.

The disposable diaper according to this invention has the first grooves and the second grooves formed in the absorbent member 38 on the side of the backsheet which is attached to the inner side of the cover member. The grooves contribute to improvement of air permeability of the absorbent member itself as well as to the air permeability between the absorbent member and the cover member so that no stuffiness is felt when the absorbent member is closely in contact with the wearer's skin.

What is claimed is:

1. A disposable diaper comprising:
   an air permeable cover member having front and rear waist regions and a crotch region; and
   a body fluid absorbent member attached to an inner surface of said cover member;
   said body fluid absorbent member extending in a longitudinal direction across said crotch region into said front and rear waist regions, said body fluid absorbent member having front and rear end portions that are fixed to the inner surface of said cover member at said front and rear end portions thereof, said body fluid absorbent member including a liquid-pervious topsheet to be placed against a wearer's body, an air permeable backsheet to be placed against said inner surface of said cover member, and a body fluid absorbent core disposed between the liquid-pervious topsheet and said backsheet, said body fluid absorbent core being formed on a side facing said backsheet with at least one groove that is concave in a direction from said backsheet toward said topsheet, each of said at least one groove consists of a first segment that extends continuously into the crotch region and the front waist region and a second segment that extends continuously into the crotch region and the rear waist region, said first and second segments of each individual ones of said at least one groove being aligned with one another longitudinally, being excluded from extending across a longitudinal center of the crotch region of the diaper, being excluded from extending into the front and rear end portions of the diaper, and being adjacent one another in the longitudinal direction but for the exclusion from the longitudinal center of the crotch region, said body fluid absorbent member having a longitudinal length that extends between and to the front and rear end portions of the diaper.

2. The disposable diaper according to claim 1, further comprising at least one groove that extends in a direction orthogonal to said longitudinal direction.

3. The disposable diaper according to claim 1, wherein said first and second segments of said at least one groove extend in said longitudinal direction and said disposable diaper further comprises at least one second groove extending in a direction orthogonal to the longitudinal direction so that said at least one second groove intersects one of said first and second segments of said at least one groove and said at least one second groove extends to transversely opposite side edges of said body fluid absorbent member.

4. The disposable diaper according to claim 3, wherein said body fluid absorbent core is disposed between said backsheet which is also formed with said at least one first groove and said at least one second groove and the topsheet opposed to said backsheet.

5. The disposable diaper according to claim 1, wherein said body fluid absorbent core is formed on a side facing said topsheet with at least one flier groove that is concave in a direction from said topsheet toward said backsheet and extends in said longitudinal direction across said crotch region into said front and rear regions.

6. The disposable diaper according to claim 5, wherein said at least one further groove is positioned to be substantially aligned with said at least one groove.

7. The disposable diaper according to claim 5, wherein said body fluid absorbent core is disposed between said topsheet which is also formed with said at least one further groove and the backsheet opposed to said topsheet.

8. The disposable diaper according to claim 1, wherein said body fluid absorbent member is detachably fixed to said cover member.

9. The disposable diaper according to claim 1, wherein said first and second segments of each individual ones of said at least one groove are collinear.

* * * * *

UNITED STATES PATENT AND TRADEMARK OFFICE
CERTIFICATE OF CORRECTION

PATENT NO. : 7,090,665 B2
APPLICATION NO. : 09/997652
DATED : August 15, 2006
INVENTOR(S) : Naoto Ohashi, Yoshio Ono and Toru Oba Page 1 of 2

It is certified that error appears in the above-identified patent and that said Letters Patent is hereby corrected as shown below:

Column 2,
Line     Line 52, should be changed from
       "leg-openings lob of which respective peripheral edge por-"
to
       --leg-openings 10b of which respective peripheral edge por- --

Column 2,
    Line 60, should be changed from
       "the cover member 2 has an hour glass shape in comprises an"
to
       --the cover member 2 has an hour glass shape and comprises an--

Column 3,
    Line 9, should be changed from
       "of the front and rear waist regions 6, 7 bu means of hot melt"
to
       --of the front and rear waist regions 6, 7 by means of hot melt--

Column 3,
    Line 25, should be changed from
       "as indicated by chin lines in FIG. 2, formed on its backsheet"
to
       --as indicated by chain lines in FIG 2, formed on its backsheet--

What is claimed:

Column 8,
Line 15, should be changed from
       "topsheet with at least one flier groove that Is concave in a"
to

UNITED STATES PATENT AND TRADEMARK OFFICE
CERTIFICATE OF CORRECTION

PATENT NO.       : 7,090,665 B2
APPLICATION NO. : 09/997652
DATED            : August 15, 2006
INVENTOR(S)      : Naoto Ohashi, Yoshio Ono and Toru Oba It is certified that error appears in the above-identified patent and that said Letters Patent is hereby corrected as shown below:

--topsheet with at least one further groove that is concave in a--

Signed and Sealed this

Twenty-eighth Day of November, 2006

JON W. DUDAS
*Director of the United States Patent and Trademark Office*